(12) United States Patent
Tesar et al.

(10) Patent No.: US 9,969,974 B2
(45) Date of Patent: May 15, 2018

(54) DIFFERNTIATION METHOD FOR PRODUCTION OF GLIAL CELL POPULATION

(71) Applicant: Case Western Reserve University, Cleveland, OH (US)

(72) Inventors: Paul J. Tesar, Wickliffe, OH (US); Robert H. Miller, Cleveland Heights, OH (US); Fadi J. Najm, University Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days. days.

(21) Appl. No.: 14/949,578

(22) Filed: Nov. 23, 2015

(65) Prior Publication Data

US 2016/0075994 A1    Mar. 17, 2016

Related U.S. Application Data

(63) Continuation of application No. 13/280,543, filed on Oct. 25, 2011, now Pat. No. 9,193,951.

(Continued)

(51) Int. Cl.
*A61K 35/30* (2015.01)
*C12N 5/079* (2010.01)

(52) U.S. Cl.
CPC ............ *C12N 5/0622* (2013.01); *A61K 35/30* (2013.01); *C12N 2501/01* (2013.01); *C12N 2501/105* (2013.01); *C12N 2501/115* (2013.01); *C12N 2501/13* (2013.01); *C12N 2501/135* (2013.01); *C12N 2501/155* (2013.01); *C12N 2501/16* (2013.01); *C12N 2501/385* (2013.01); *C12N 2501/41* (2013.01); *C12N 2501/727* (2013.01); *C12N 2506/02* (2013.01)

(58) Field of Classification Search
None
See application file for complete search history.

(56) References Cited

U.S. PATENT DOCUMENTS

| | | | |
|---|---|---|---|
| 2002/0164308 A1* | 11/2002 | Reubinoff | C12N 5/0619 424/93.7 |
| 2005/0101014 A1* | 5/2005 | Keirstead | C12N 5/0622 435/373 |

(Continued)

FOREIGN PATENT DOCUMENTS

| | | |
|---|---|---|
| WO | 2008/056166 | 5/2008 |
| WO | 2008/056173 A2 | 5/2008 |
| WO | 2010/108005 | 9/2010 |

OTHER PUBLICATIONS

Magy, Laurent; et al; "Transient exposure to FGF2 enhances myelination in embryonic brain cell cocultures" Experimental Neurobiology, 181, 17-24, 2003.*

(Continued)

*Primary Examiner* — David W Berke-Schlessel
(74) *Attorney, Agent, or Firm* — McCarter & English, LLP; Steven G. Davis

(57) ABSTRACT

The present invention provides methods for generating oligodendrocyte progenitor cells from pluripotent cells, as well as methods for sustaining these oligodendrocyte progenitor cells in relatively pure cultures for long periods of time. The present invention also provides methods for further differentiating these oligodendrocyte progenitor cells into various glial cells.

12 Claims, 5 Drawing Sheets

Related U.S. Application Data

(60) Provisional application No. 61/406,664, filed on Oct. 26, 2010.

(56) References Cited

U.S. PATENT DOCUMENTS

| | | |
|---|---|---|
| 2010/0034785 A1 | 2/2010 | Pedersen et al. |
| 2013/0022583 A1 | 1/2013 | Wernig et al. |

OTHER PUBLICATIONS

Yang, Zhongshu; et al; "Optimization of oligodendrocyte progenitor cell culture method for enhanced survival" Journal of Neuroscience Methods, 149, 50-56, 2005.*

Nistor, Gabriel I; et al; "Human Embryonic Stem Cells Differentiate into Oligodendrocytes in High Purity and Myelinate After Spinal Cord Transplantation" Glia, 49, 385-396, 2005).*

Hu and Zhang, Differentiation of spinal motor neurons from pluripotent human stem cells, Nature Protocols, 4(9):1295-1304 (2009).

Sundberg, et al., Production and isolation of NG2+ oligodendrocyte precursors from human embryonic stem cells in defined serum-free medium, Stem Cell Research, 5:91-103 (2010).

Neman and De Vellis, A Method for Deriving Homo~enous Population of 0/igodendrocytes from Mouse Embryonic Stem Cells, Developmental Neurobiology, ublished online Jan. 11, 2012, pp. 777-788.

Lu, et al., Proliferation and Differentiation of Oligodendrocyte Progenitor Cells Induced from Rat Embryonic Neural Precursor Cells Followed by Flow Cytometry, Cytometry, 73A:754-60 (2008).

Keirstead, et al., Human Embryonic Stem Ce/I-Derived Oligodendrocyte Progenitor Cell Transplants Remyelinate and Restore Locomotion after Spinal Cord Injury, J. of Neuroscience, 25(19):4694-705 (2005).

Gonzalez, et al., Generation of mouse-induced plur-otent stem cells by transient expression of a single nonviral polycistronic vector, PNAS, 106(22):8918-22 2009).

Kim, et al., Generation of Human Induced Pluripotent Stem Cells by Direct Delivery of Reprogramming Proteins, Cell Stem Cell, 4:472-76 (2009).

Zhou, et al., Generation of Induced Pluripotent Stem Cells Using Recombinant Proteins, Cell Stem Cell, 4:381-84 (2009).

Stadtfeld, et al., Induced Pluripotent Stem Cells Generated Without Viral Integration, 322:945-49 (2008).

Stadtfeld and Hochedlinger, Review: Induced pluripotency, history, mechanisms, and applications, Genes and Development, 24:2239-63 (2010).

Okita, et al., Generation of Mouse Induced Pluripotent Stem Cells Without Viral Vectors, Science, 322:949-53 (2008).

Denham and Dottori, Signals Involved in Neural Differentiation of Human Embryonic Stem Cells, Neuro-Signals, 17:234-41 (2009).

Nonfinal Office Action dated Dec. 14, 2013 for U.S. Appl. No. 13/280,562, pp. 1-85.

Lu, Q. Richard; et al; "Sonic Hedgehog-Regulated Oligodendrocyte Lineage Genes Encoding bHLH Proteins in the Mammalian Central Nervous System" Neuron, 25, 317-329, 2000.

Zhang, Zhi-Jian; et al; "Neural Differentiation" Human Cell Culture, vol. VI, Chapter 6, 2007.

Erceg, Slaven; et al; "Human Embryonic Stem Cell Differentiation Toward Regional Specific Neural Precursors" Stem Cells, 27, 78-87, 2009.

Du, Zhong-Wei; Zhang, Su-Chun; "Neural Differentiation from Embryonic Stem Cells: Which Way?" Stem Cells and Development, 13, 372-381, 2004.

Lu et al "Cyclosporin A increases recovery after spinal cord injury but does not improve myelination by oligodendrocyte progenitor cells transplantation", BMC Neuroscience, 11 (127):1-16 (2010).

Niajm, et al, "Rapid and robust generation of functional oligodendrocyte progenitor cells from epiblast stem cells", Nature Methods, 8(11):957-62 (2011).

Nakashima, et al., "Astrocyte differentiation mediated by LIF in cooperation with BMP2", FEBS Letters, 457:43-49 (1999).

Vallier,et al., "Early cell fate decisions of human embryonic stem cells and mouse epiblast stem cells are controlled by the same signalling pathways", PLoSone, 4(6):e6082:1-3 (2009).

Vierbuchen, et al., "Direct conversion of fibroblasts to functional neurons by defined factors", Nature, 463:1035-41 (2010).

Zhang, et al., "Increase myelinating capacity of embryonic stem cell derived oligodendrocyte precursors after treatment by interleukin-6/soluble interleukin-6 receptor fusion protein", Molecular and Cellular Neuroscience, 31_387-98 (2005).

Zhang, et al., "Increase myelinating capacity of embryonic stem cell derived oligodendrocyte precursors after treatment by interleukin-6/soluble interleukin-6 receptor fusion protein", Molecular and Cellular Neuroscience, 31_387-98 (2005) (Supplement).

Written Opinion of the International Searching Authority for PCT/US2011 /057762 dated May 7, 2012.

Written Opinion of the International Searching Authority for PCT/US2012/057759 dated Mar. 29, 2013.

Yamanaka, Strategies and New Developments in the Generation of Patient-Specific Pluripotent Stem Cells, Cell Stem Cell, 4:472-76 (2009).

* cited by examiner

DIFFERNTIATION METHOD FOR PRODUCTION OF GLIAL CELL POPULATION

CROSS-REFERENCE TO RELATED APPLICATIONS

This application claims the benefit of U.S. Provisional Patent Application No. 61/406,664, filed Oct. 26, 2010 as is incorporated herein by reference.

STATEMENT OF GOVERNMENT SPONSORED RESEARCH

This invention was supported in part by grant R21MH087877-01 from the National Institute of Mental Health (NIMH). The Federal Government has certain rights in this invention.

FIELD OF THE INVENTION

This invention relates to the production of cells and homogeneous cell populations of glial lineage.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Effective conduction of action potentials in the mammalian central nervous system (CNS) requires proper ensheathment and insulation of neuron axons by myelin. Impairments of oligodendrocyte cells, the myelinogenic cells of the mammalian CNS, cause a number of debilitating and often fatal human conditions. The incapacitating effects of myelin defects are typified by motor and sometimes cognitive deficiencies and are readily apparent in congenital dysmyelinating disorders as well as acquired demyelinating conditions such as multiple sclerosis and cerebral palsy. Treatment via remyelination necessitates either the restoration of the myelinating capacity of endogenous cells or transplantation of exogenous, myelinating cells.

Transplantation of fetal human glial progenitor cells has been shown to lead to recovery in a lethally hypomyelinated mouse model (Windrem, et al., Cell Stem Cell, 2(6):553-65 (2008). While clearly establishing proof-of-principle for translation to human patients, cells from aborted human fetuses not only face ethical and immunological challenges; however, providing the number of cells needed on a clinical scale currently is not realistic. Thus, a major limiting factor to the understanding and treatment of myelin-related neurodegenerative disorders is the lack of a scalable and tractable platform for the study of oligodendrocyte development and for screening of pharmaceuticals.

Stem cell biology has garnered much attention due to the potential to impact human health through disease modeling and cell replacement therapy. Pluripotent stem cells in particular theoretically offer an abundant source of glial cells and their progenitors. While previous studies have created excitement for myelin repair by clearly demonstrating that oligodendrocytes can be derived from pluripotent cells, results have yet to yield a system to study oligodendrocyte lineage that provides high cell population homogeneity without reliance on immunopanning, antibiotic resistance, or cell sorting techniques to improve population characteristics. The excitement for myelin repair has thus been tempered since pure populations of oligodendrocyte progenitor cells (OPCs) are difficult to obtain in clinically-relevant quantities. Methods for providing pure and plentiful glial cells are necessary to enable therapy through transplantation.

There is thus a need in the art for production of cells and cell populations of the glial lineages, and in particular for OPCs and oligodendrocytes. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides methods for generating glial cells comprising growing mammalian pluripotent cells and/or neural precursor cells under conditions that induce differentiation of the mammalian pluripotent cells and/or neural precursor cells into cells and cell populations of the glial lineage. The present invention also provides methods for the generation, expansion and use of populations of mammalian glial cells, including populations of oligodendrocyte progenitor cells, oligodendrocytes, and astrocytes. Moreover, the production of oligodendrocyte progenitor cells, oligodendrocytes, and astrocytes by the methods described herein requires far less time than methods used in the art currently.

Thus, the in one embodiment, the present invention provides a method for generating mammalian neuroectoderm comprising: providing pluripotent cells; and inducing development of the pluripotent cells into neuroectoderm cells by culturing the pluripotent cells in the presence of one or more inhibitors of an activin-nodal pathway and one or more inhibitors of a bone morphogenetic protein pathway.

In another embodiment, the present invention provides a method for generating mammalian patterned neuroectoderm comprising: providing a pluripotent cell; inducing development of the pluripotent cell into neuroectoderm by culturing the pluripotent cell in the presence of one or more inhibitors of an activin-nodal pathway and one or more inhibitors of a bone morphogenetic protein pathway; and inducing development of patterned neuroectoderm by culturing the neuroectoderm in the presence of one or more of sonic hedgehog, retinoic acid and noggin.

In yet another embodiment, the present invention provides a method for generating mammalian oligodendrocyte progenitor cells comprising: providing a pluripotent cell; inducing development of the pluripotent cell into neuroectoderm by culturing the pluripotent cell in the presence of one or more inhibitors of an activin-nodal pathway and one or more inhibitors of a bone morphogenetic protein pathway; inducing development of patterned neuroectoderm by culturing the neuroectoderm in the presence of one or more of sonic hedgehog, retinoic acid and noggin; and inducing development of oligodendrocyte progenitor cells by culturing the patterned neuroectodermal cells in the presence of one or more of a fibroblast growth factor, a platelet-derived growth factor and sonic hedgehog.

In some aspects of these embodiments, the pluripotent cell is a mammalian epiblast stem cell, and in other aspects the pluripotent cell is a neural precursor cell. In some embodiments, the pluripotent cell is a rodent embryonic stem cell (ESC) or a rodent induced pluripotent cell (iPC), in which case the rodent ESCs or iPCs are first cultured in the presence of a JAK/STAT inhibitor, such as JAK Inhibitor I, to differentiate the cells into an epiblast-like cell before continuing differentiation to neuroectoderm.

In some aspects of these embodiments, the inhibitor of the activin-nodal pathway is SB431542, and the one or more inhibitors of the bone morphogenetic protein pathway is selected from dorsomorphin, LDN-193189 or noggin. In some aspects of these embodiments, 75% or more of cells resulting from the culture of the pluripotent cells are neuroectoderm cells, and in other aspects, 80%, 85%, 90%, 95%, 99% or more of cells resulting from the culture of the pluripotent cells are neuroectoderm cells.

In some aspects, one of retinoic acid, sonic hedgehog or noggin is used in the culture of the neuroectoderm to produce patterned neuroectoderm, and in some aspects two of retinoic acid, sonic hedgehog or noggin are used in the culture of the neuroectoderm to produce patterned neuroectoderm. In yet other aspects all three of retinoic acid, sonic hedgehog and noggin are used in the culture of the neuroectoderm to produce patterned neuroectoderm. In some aspects, one or more of a fibroblast growth factor, a platelet-derived growth factor and sonic hedgehog are used to induce development of oligodendrocyte progenitor cells from the patterned neuroectoderm, and in other aspects, all three of a fibroblast growth factor, a platelet-derived growth factor and sonic hedgehog are used to induce development of oligodendrocyte progenitor cells from patterned neuroectoderm. In some aspects, the fibroblast growth factor is PGF2 and the platelet-derived growth factor is PDGF-AA. neuroectoderm. In some aspects of these embodiments, 75% or more of cells resulting from the culture of the patterned neuroectoderm are oligodendrocyte progenitor cells, and in other aspects, 80%, 85%, 90%, 95%, 99% or more of cells resulting from the culture of the patterned neuroectoderm are oligodendrocyte progenitor cells.

Further aspects of the invention include pharmaceutical compositions comprising the oligodendrocyte progenitor cells of the invention, pharmaceutical compositions comprising the oligodendrocyte progenitor cells of the invention along with neurons or neuron precursor cells, diagnostic tools comprising the oligodendrocyte progenitor cells of the invention, and research tools comprising the oligodendrocyte progenitor cells of the invention. Yet other aspects include treating a medical condition of the CNS in a subject comprising administering to the subject a therapeutically effective amount of the oligodendrocyte progenitor cells produced by methods of the invention.

Yet another embodiment of the invention provides a method for generating mammalian oligodendrocyte progenitor cells and maintaining the mammalian oligdendrocyte progenitor cells in culture comprising: providing a pluripotent cell; inducing differentiation of the pluripotent cell into neuroectoderm by culturing the pluripotent cell in the presence of one or more inhibitors of an activin-nodal pathway and one or more inhibitors of a bone morphogenetic protein pathway; inducing development of patterned neuroectoderm by culturing the neuroectoderm in the presence of one or more of sonic hedgehog, retinoic acid and noggin; and inducing development of oligodendrocyte progenitor cells by culturing the patterned neuroectoderm in the presence of a fibroblast growth factor, a platelet-derived growth factor and sonic hedgehog; and maintaining the oligodendrocyte progenitor cells by culturing the oligodendrocyte cells in the presence of an activator of Wnt-β-catenin signaling or in the presence of fibroblast growth factor (FGF), platelet-derived growth factor (PDGE) and sonic hedgehog (SHH).

In some aspects of this embodiment of the invention, 75% or more of cells resulting from the culture of the patterned neuroectoderm are oligodendrocyte progenitor cells, and in other aspects, 80%, 85%, 90%, 95%, 99% or more of cells resulting from the culture of the patterned neuroectoderm are oligodendrocyte progenitor cells. In some aspects, 75% or more of cells in the maintained culture of the oligodendrocyte progenitor cells are oligodendrocyte progenitor cells, and in other aspects, 80%, 85%, 90%, 95%, 99% or more of cells in the maintained culture of the oligodendrocyte progenitor cells are oligodendrocyte progenitor cells. In some aspects of this embodiment of the invention, the activator of Wnt-β-catenin signaling is a GSK3β inhibitor, and in specific aspects, the GSK3β inhibitor is CHIR99021.

Additional aspects of this embodiment of the invention include methods for generating oligodendrocytes from the oligodendrocyte progenitor cells maintained in culture, comprising culturing the oligodendrocyte progenitor cells in the absence of FGF and PDGF and in the presence of a factor to promote differentiation. In some aspects the oligodendrocyte differentiation activator is thyroid hormone (T3). Additional aspects of this embodiment of the invention include methods for generating astrocytes from the oligodendrocyte progenitor cells maintained in culture, comprising culturing the oligodendrocyte progenitor cells in the presence of a bone morphogenetic protein and a JAK/STAT pathway activator.

Other embodiments and aspects of the invention are described in the Detailed Description below.

DEFINITIONS

Figure 1:
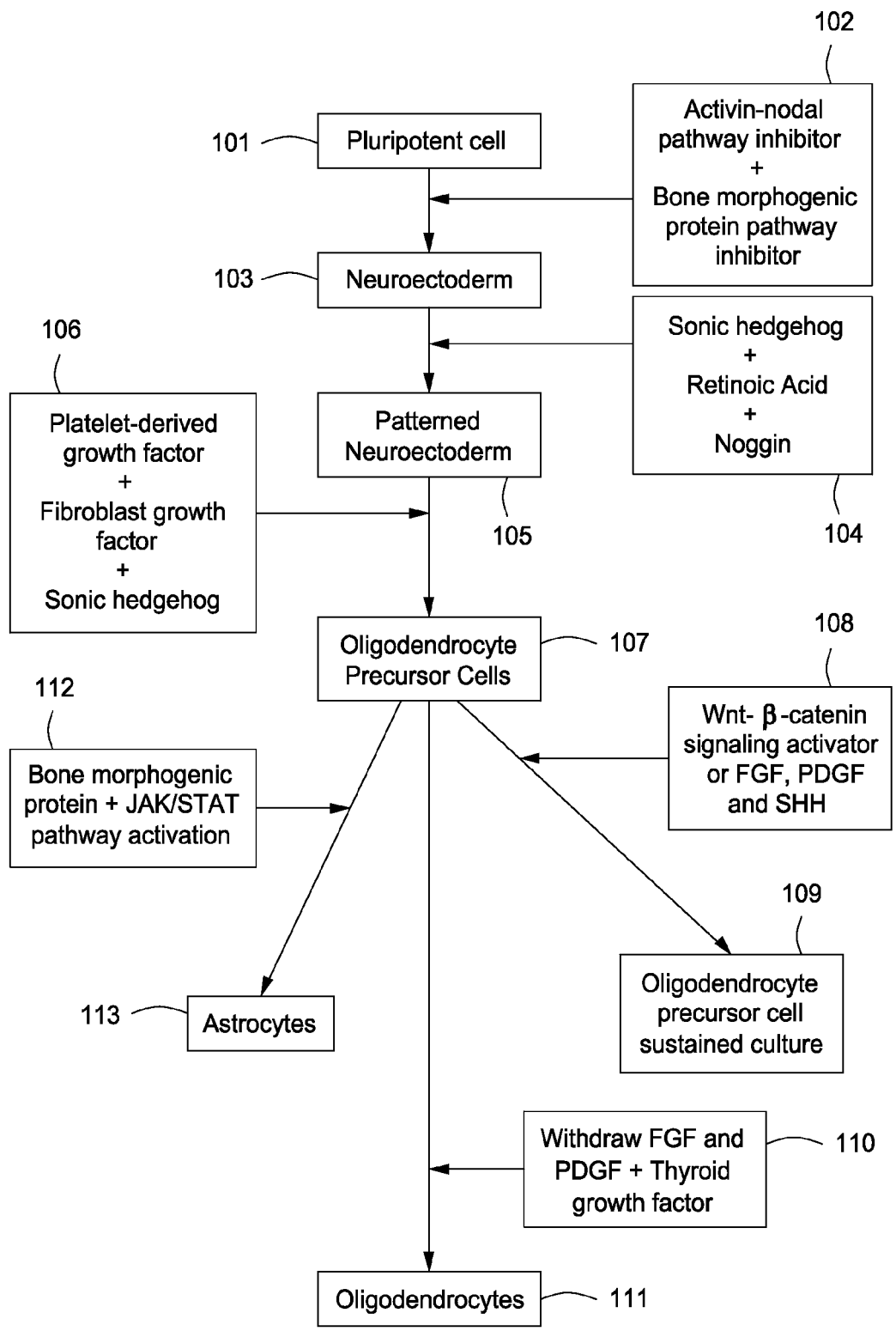
FIG. 1 is a general schematic showing the steps of directed differentiation of pluripotent cells into cells of the oligodendrocyte cell fate.

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The terms "astrocytes" and "astroglia" refer to glial cells that anchor neurons to their blood supply. Astrocytes of the present invention refer to both protoplasmic and fibrous astrocytes. Astrocytes of the present invention are characterized by expression of one or more of glial fibrillary acidic protein (GFAP), S100 beta, glutamine sythetase, GLAST or GLT1 and have at least one astrocytic structural or functional phenotype. Astrocytic structural phenotypes include a round nucleus, a "star shaped" body and many long processes that end as vascular foot plates on the small blood vessels of the CNS; further examples of structural astrocytic phenotypes may be found in the following materials: Reynolds and Weiss, Science, 255:1707-1710 (1992); Reynolds, et al., J. Neurosci, 12:4565-4574 (1992); and Kandel, et al., Principles of Neuroscience, Third Ed. (1991) (Appleton & Lange).

A "binding agent" is any molecule that binds to one or more regions on or in a cell of a particular cell fate via association by chemical or physical means. For the purposes of the present invention, a binding agent preferably selectively interacts with a cell surface molecule or intracellular protein or moiety that is unique to cells of a particular cell fate, e.g., oligodendrocyte progenitor cells. Examples of binding agents that can be used in this invention include, but are not restricted to: peptides, proteins (including derivatized or labeled proteins); antibodies or fragments thereof; small molecules; aptamers; carbohydrates and/or other non-protein binding moieties; derivatives and fragments of naturally-occurring binding partners; peptidomimetics; and pharmacophores.

The term "biological process" as used herein includes both normal physiological processes, such as remyelination, neuroprotection, etc., as well as pathological processes, e.g., those involved in diseases and conditions such as autoimmune diseases, neurodegenerative diseases, diseases involving genetic dysfunction, and the like.

The term "diagnostic tool" as used herein refers to any composition or assay of the invention used in order to carry out a diagnostic test or assay on a patient sample. As a diagnostic tool, the composition of the invention may be considered a collection of analyte specific reagents, and as such may form part of a diagnostic test regulated by a federal or state agency.

The term "excipient" refers to an inert substance added to a pharmaceutical composition of the invention to further facilitate administration of the therapeutic cells. Examples, without limitation, of excipients include saline, calcium carbonate, calcium phosphate, various sugars and types of starch, cellulose derivatives, gelatin, vegetable oils and polyethylene glycols.

The term "glial cells" and "glia" refer to non-neuronal precursor and/or fully-differentiated cells in the nervous system that provide support and nutrition, maintain homeostasis, form myelin, and participate in signal transmission. Examples of glial cells of the present invention include but are not limited to oligodendrocyte progenitor cells, oligodendrocytes and astrocytes.

The terms "introducing", "introduction" and the like when used in the context of delivery of an agent to a cell (e.g., a wnt pathway activator or a activin-nodal pathway inhibitor) refer to the delivery of the agent in any biologically effective form, including but not limited to peptides, proteins (including derivatized or labeled protein), antibodies or fragments thereof, small molecules, aptamers, peptidomimetics, and/or pharmacophores. The term "introducing" is also intended to encompass the introduction through genetic means, e.g., the introduction of a gene expression vector such as a viral vector (e.g., an adenoviral vector or a lentiviral vector) or an epigenetic vector.

The term "oligodendrocyte" refers to mature well-differentiated oligodendrocytes. Mature oligodendrocytes may be distinguished from oligodendrocyte progenitor cells both by structural and functional phenotypes. Examples of mature oligodendrocyte functional phenotypes include but are not limited to expression of one or more markers such as proteolipid protein (PLP), myelin basic protein (MBP), myelin-associated glycoprotein (MAG), myelin oligodendrocyte glycoprotein (MOG), and/or one or more galactocerebrosides (O1, GalC). Examples of mature oligodendrocyte structural phenotypes include but are not limited to, a branched and ramified phenotype and the ability to effect myelination.

The terms "oligodendrocyte progenitor cells" and "OPCs" as used herein refer to cells that have the capacity to differentiate into oligodendrocytes. OPCs may be distinguished from oligodendrocytes both by structural and functional phenotypes. Examples of an oligodendrocyte progenitor cell functional phenotype include, but are not limited to, cells that are mitotic (i.e., that can divide and be expanded for three or more passages in culture), have migratory capacity, and the potential to differentiate into a myelinating phenotype to effect myelination in vivo and in vitro.

The term "pharmaceutical composition" refers to a preparation of one or more of the cells of the invention described herein, with at least one pharmaceutically suitable excipient.

The term "pharmaceutically acceptable carrier" refers to a carrier or a diluent that facilitates delivery and/or the biological activity and properties of the administered cells. Examples without limitation of carriers are propylene glycol, saline, emulsions and mixtures of organic solvents with water.

The term "pluripotent cells" refers to cells that are capable of both differentiating into more specialized cell types (e.g., glial cells) having a particular, specialized function (i.e., "fully differentiated" cells) and the ability to give rise to cells having the same or similar undifferentiated state.

The term "research tool" as used herein refers to any cell composition of the invention or use of the cells or cell compositions of the invention for scientific inquiry, either academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

The term "selectively binds," "selective binding" and the like as used herein, when referring to a binding partner (e.g., protein, nucleic acid, antibody, etc.), refers to a binding reaction which is determinative of the presence of a composition (typically a cell marker) in heterogeneous population of molecules (e.g., proteins and other biologics). Thus, under designated assay conditions, the binding partner will bind to a composition of the invention at least two times the background and will not substantially bind in a significant amount to other compositions (cell markers) present in the sample. Typically, specific binding will be at least five times background signal or noise and more typically more than 10 to 100 times background. Thus, under designated conditions the binding partner binds to its particular "target" composition and does not bind in a significant amount to other molecules present in the sample.

The term "small molecule" as used herein refers to a molecule of a size comparable to those organic molecules generally used in chemistry-based pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

DETAILED DESCRIPTION OF THE INVENTION

The practice of the techniques described herein may employ, unless otherwise indicated, conventional techniques and descriptions of organic chemistry, polymer technology, molecular biology (including recombinant techniques), cell biology, mammalian cell culture, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Butler (2004), *Animal Cell Culture* (BIOS Scientific); Picot (2005), *Human Cell Culture Protocols* (Humana Press), Davis (2002), *Basic Cell Culture*, Second Ed. (Oxford Press); Lanza, et al., (Eds.) (2009), *Essentials of Stem Cell Biology*, Second Ed. (Elsevier Academic Press); Lanza, (Ed.) (2009), *Essential Stem Cell Methods* (Elsevier Academic Press); Loring, et al. (Eds.) (2007), *Human Stem Cell Manual* (Elsevier Academic Press); Freshney (2010), *Culture of Animal Cells* (John Wiley & Sons); Ozturk and Hu (2006), *Cell Culture Technology for Phamaceutical and Cell-Based Therapies* (CRC Press); Sambrook and Russell (2006), *Condensed Protocols from Molecular Cloning: A Laboratory Manual*; and Sambrook and Russell (2002), *Molecular Cloning: A Laboratory Manual* (both from Cold Spring Harbor Laboratory Press); Stryer, L. (1995) *Biochemistry*, Fourth Ed. (W.H. Freeman); Nelson and Cox (2000), *Lehninger, Principles of Biochemistry*, Third Ed. (W. H. Freeman); and Berg et al. (2002) *Biochemistry*, Fifth Ed. (W. H. Freeman); all of which are herein incorporated in their entirety by reference for all purposes.

Note that as used herein and in the appended claims, the singular forms "a," "an," and "the" include plural referents unless the context clearly dictates otherwise. Thus, for example, reference to "an oligodendrocyte progenitor cell" refers to one or more cells of glial cell fate, and reference to "sorting" or "inducing" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention.

Culture Methods of the Invention to Differentiate and Create Cell Populations

The present invention is based on the novel discovery that pluripotent stem cells can be differentiated through a defined series of developmental transitions into cells and cell populations of the glial lineage, recapitulating the complex signaling environment present in the developing embryo. This includes differentiating pluripotent stem cells into relatively pure populations of expandable cells including OPCs, oligodendrocytes and astrocytes. The methods provide the ability to create large quantities of cells of the glial lineage, including oligodendrocyte progenitor cells from pluripotent stem cells. Such OPCs can then be either expanded into additional OPCs or further differentiated into mature cells such as oligodendrocytes and astrocytes. These glial cells can be differentiated directly from pluripotent cells, or they may be generated from existing neural precursor cells that are already partially driven down the ectodermal cell fate pathway.

FIG. 1 is a general schematic showing the steps of a method 100 for directed differentiation of pluripotent cells into expandable populations of OPCs, myelinating oligodendrocytes, and astrocytes. At 101, pluripotent cells are provided. Numerous types of pluripotent cells can be used in the methods of the present invention. The pluripotent cells are preferably mammalian stem cells, although in certain aspects avian pluripotent cells may be used in the generation of the cells and cell populations of the invention.

In some aspects of the invention, the pluripotent cells are rodent pluripotent cells. Such rodent pluripotent cells include rat or mouse induced pluripotent cells, rat or mouse embryonic stem cells (mES cells), such as those described in or derived as described in, e.g., U.S. Pat. No. 6,190,910; rat or mouse epiblast-derived stem cells (EpiSCs), such as those described in USSN 2010/0064380 and Tesar, et al., Nature, 448(7150):196-9 (2007), Epub Jun. 27, 2007, both of which are incorporated herein by reference; rat or mouse induced epiblast stem cells, rodent embryonic germ cells (EGCs) that have been derived from primordial germ cells (PGCs) of the midgestation embryo (Matsui, et al., Cell, 70(5):841-7 (1992); Resnick, et al., Nature, 359(6395):550-1 (1992); and multipotent germline stem cells (mGSCs) that have been generated from explanted neonatal testicular cells (Kanatsu-Shinohar,a et al., Cell, 119(7):1001-12 (2004)), adult testicular cells (Guan, et al., Nature, 440(7088):1199-203

(2006), Epub Mar. 24, 2006; Seandel, et al., Nature; 449 (7160):346-50 (2007); Ko, et al., Cell Stem Cell, 5(1):87-96 (2009)), or mouse testicular cells. In the case of rodent embryonic stem cells or rodent induced pluripotent cells, the cells are first differentiated into an epiblast state using, e.g., growth in a culture medium containing a JAK/STAT inhibitor such as JAK Inhibitor I for two to four days.

In certain aspects, the pluripotent cells are derived from rodent strains with clinically relevant genotypes, e.g., mice having specific mutations or polymorphisms associated with clinical sensitivities or pathologies in humans. Mouse embryonic stem cells having various mutations or polymorphisms allow the production of glial cells with these mutations, which are useful in studying disease progression and producing cell populations, e.g., for identifying therapeutic candidate agents or toxicity testing of candidate or existing therapeutic agents.

In other aspects, other mammalian pluripotent cells may be utilized, depending on e.g., the mammal to be treated or the animal model of interest. Such mammals include cats, dogs, horses, pigs, cows, sheep, etc., and primates.

In other aspects, the pluripotent cells used in the methods of the invention are human cells. For example, human embryonic stem cells can be isolated from human blastocysts or derived from a delayed blastocyst stage (e.g., those described in WO2006/040763). Pluripotent cell lines have also been derived from other embryonic and adult tissues upon explantation in culture, and techniques are known in the art for preparing such human induced or derived pluripotent cells. Common to all of these cell types is their origin from either early embryos or germ lineage cells, which appear to be the only cells that harbor an epigenetic conformation that is permissive for spontaneous conversion into a pluripotent state. A molecular commonality among these cell types is the expression of endogenous Oct4, which may thus serve as a valuable predictive marker for whether or not a cell can give rise to pluripotent cell lines useful to generate the OPCs, OPC populations, oligodendrocytes and astrocytes of the invention. In some cases of human embryonic stem cells or human induced pluripotent cells, the cells are first differentiated into an epiblast state using, e.g., growth in a culture medium containing a JAK/STAT inhibitor such as JAK Inhibitor I for two to four days.

Stem cells for use in the present invention also may be derived from human embryonic germ (EG) cells. For additional details on methods of preparation human embryonic germ cells see Shamblott et al., PNAS USA, 95: 13726 (1998) and U.S. Pat. No. 6,090,622. In certain aspects, the pluripotent cells used for differentiation of the cells and cell populations of the glial cell lineage are induced pluripotent stem cells, such as those as described in Tokuzawa et al., Cell, 113(5):631-42 (2003).

At step 102, one or more activin-nodal pathway inhibitors and one or more bone morphogenetic protein pathway inhibitors are added to the culture medium of the pluripotent cells 101. Cell culture techniques are well known in the art, with reference to such text books as Butler (2004), *Animal Cell Culture* (BIOS Scientific); Picot (2005), *Human Cell Culture Protocols* (Humana Press); Davis (2002), *Basic Cell Culture*, Second Ed. (Oxford Press); Freshney (2010), *Culture of Animal Cells* (John Wiley & Sons); and Ozturk and Hu (2006), *Cell Culture Technology for Phamaceutical and Cell-Based Therapies* (CRC Press). For example, the pluripotent cells may be epiblast stem cells, where the medium for culture comprises Knockout DMEM supplemented with 20% Knockout Serum Replacement, Glutamax, nonessential amino acids and 0.1 mM 2-mercaptoethanol (Sigma-Aldrich, St. Louis, Mo.), or other media known in the art.

The one or more activin-nodal pathway inhibitors and one or more bone morphogenetic protein pathway inhibitor are added to (are "introduced to") this culture medium. Nodal is a protein that in humans is encoded by the NODAL gene, and is a member of the Transforming Growth Factor beta superfamily. Like many other members of the TGF beta superfamily, Nodal is involved in cell differentiation. Studies of the mouse counterpart of NODAL suggest that this gene may be essential for mesoderm formation and subsequent organization of left-right axial structures in early embryonic development. A Nodal knockout in mice causes precocious differentiation to neuroectoderm and an absence of the primitive streak and failure in formation of mesoderm, leading to developmental arrest just after gastrulation. Activin-nodal signaling contributes to maintaining pluripotency of human embryonic stem cells (hESCs), which are derivatives of the inner cell mass but share molecular properties with epiblast tissue. Inhibition of activin-nodal signaling results in the loss of hESC pluripotency. Examples of inhibitors of the activin-nodal pathway include but are not limited to SB431542, SB505124, A83-01, and follistatin.

Bone Morphogenetic Proteins (BMPs) are a family of ligands that also belong to the TGF beta superfamily. BMPs interact with specific receptors on a cell surface, referred to as bone morphogenetic protein receptors. Signal transduction through BMPRs results in phosphorylation of downstream targets. The best characterized signaling cascade is the Smad pathway, shown to be important in the development of the heart, central nervous system, and cartilage, as well as post-natal bone development. Mutations in BMPs and their antagonists, for example Sclerostin, are associated with a number of human disorders that affect the skeleton and other tissues. Examples of bone morphogenetic protein pathway inhibitors include but are not limited to Dorsomorphin, LDN-193189, noggin, ALK3-Fc, ALK6-Fc, Gremlin, Chordin, and Cerberus.

Treatment of pluripotent cells, such as pluripotent epiblast stem cell, with an activin-nodal pathway inhibitor such as SB431542, an inhibitor of TGF beta superfamily Type I Activin receptor-like kinase (ALK) receptors ALK4, ALK5, and ALK7 (see Inman, et al., Molecular Pharmacology, 62(1):65-74 (2002)) and a bone morphogenetic protein pathway inhibitor such as Dorsomorphin, a selective small molecule inhibitor of BMP signaling (see, Yu, et al., Nat Chem Biol, 4: 33-41 (2008)) results in region-specific neuroectodermal cell differentiation 103. The resulting neuroectoderm can then be further differentiated into patterned neuroectoderm 105 by culture in the presence of one or more of sonic hedgehog (SHH), retinoic acid (RA) and noggin at step 104, which results in the upregulation of region-specific transcription factors Olig2 and Nkx2.2, which are normally expressed in the ventral region of the developing neural tube. Differentiation to oligodendrocyte progenitor cells is achieved by culturing the neuroepithelial cells in the presence of a platelet-derived growth factor (PDGF), a fibroblast growth factor (FGF) and sonic hedgehog (SHH) at 106

Sonic hedgehog homolog (SHH) is one of three proteins in the mammalian signaling pathway family called hedgehog, the others being desert hedgehog and Indian hedgehog. SHH is the best studied ligand of the hedgehog signaling pathway, playing a key role in regulating vertebrate organogenesis, such as in the growth of digits on limbs and organization of the brain. Sonic hedgehog is one of the best established example of a morphogen—a molecule that diffuses to form a concentration gradient having different effects on the cells of the developing embryo depending on its concentration. Sonic hedgehog assumes various roles in patterning the central nervous system (CNS) during vertebrate development, and remains important in the adult, controlling cell division of adult stem cells. More recently, sonic hedgehog has also been shown to act as an axonal guidance cue Retinoic acid (RA) is a metabolite of vitamin A (retinol) that mediates the functions of vitamin A required for growth and development. Retinoic acid is required in chordate animals which includes all higher animals from fishes to humans. During early embryonic development, retinoic acid generated in a specific region of the embryo helps determine position along the embryonic anterior/posterior axis by serving as an intercellular signaling molecule that guides development of the posterior portion of the embryo. It acts through Hox genes, which ultimately control anterior/posterior patterning in early developmental stages.

Noggin, also known as NOG, is a protein which in humans is encoded by the NOG gene. Noggin inhibits TGF-β signal transduction by binding to TGF-β family ligands and preventing them from binding to their corresponding receptors. Noggin plays a key role in neural induction by inhibiting BMP4, along with other TGF-β signaling inhibitors such as chordin and follistatin. Mouse knockout experiments have demonstrated that noggin also plays a crucial role in bone development, joint formation, and neural tube fusion. The secreted polypeptide noggin, encoded by the NOG gene, binds and inactivates members of the transforming growth factor-beta superfamily signaling proteins, such as bone morphogenetic protein-4. Noggin appears to have pleiotropic effect, both early in development as well as in later stages.

Platelet-derived growth factor (PDGF) is one of numerous growth factors that regulate cell growth and division, playing a significant role in angiogenesis, embryonic development, cell proliferation, and cell migration. In chemical terms, platelet-derived growth factor is dimeric glycoprotein composed of two A (-AA) or two B (-BB) chains or a combination of the two (-AB). PDGFs are mitogenic during early developmental stages, driving the proliferation of undifferentiated mesenchyme and some progenitor populations. During later maturation stages, PDGF signaling has been implicated in tissue remodeling and cellular differentiation, and in inductive events involved in patterning and morphogenesis. In addition to driving mesenchymal proliferation, PDGFs have been shown to direct the migration, differentiation and function of a variety of specialized mesenchymal and migratory cell types, both during development and in the adult animal. Other growth factors in this family include vascular endothelial growth factors B and C, and placenta growth factor (P1GF).

Fibroblast growth factors, or FGFs, are a family of growth factors involved in angiogenesis, wound healing, and embryonic development. FGFs are multifunctional proteins with a wide variety of effects; they are most commonly mitogens but also have regulatory, morphological, and endocrine effects. They have been alternately referred to as "pluripotent" growth factors and as promiscuous growth factors due to their multiple actions on multiple cell types. In the case of FGF, four receptor subtypes can be activated by more than twenty different FGF ligands. The functions of FGFs in developmental processes include mesoderm induction, antero-posterior patterning, limb development, neural induction and neural development, and in mature tissues/systems angiogenesis, keratinocyte organization, and wound healing processes.

The oligodendrocyte progenitor cells 107 formed from the patterned neuroectoderm in method 100 can be maintained in culture without differentiation through the introduction of a Wnt pathway activator, preferably using one or more GSK3β inhibitors, or by culture in the presence of fibroblast growth factor (FGF), platelet-derived growth factor (PDGF) and sonic hedgehog (SHH) at 108. Exemplary GSK3β inhibitors that may be used in the methods of the invention include, but are not limited to, lithium chloride (LiCl), 6-bromoindirubin-3'-oxime (BIO), Chiron 99021 and those compounds described in U.S. Pat. No. 7,300,943 to Gabriel, et al., which is incorporated herein by reference in its entirety. The Wnt signaling pathway is a network of proteins best known for their roles in embryogenesis and cancer, but also involved in normal physiological processes in adult animals. Wnt proteins activate various pathways in the cell that can be categorized into the canonical and noncanonical Wnt pathways. The canonical Wnt pathway describes a series of events that occur when Wnt proteins bind to cell-surface receptors of the Frizzled family, causing the receptors to activate Disheveled family proteins, ultimately resulting in a change in the amount of β-catenin that reaches the nucleus. Disheveled is a key component of a membrane-associated Wnt receptor complex, which, when activated by Wnt binding, inhibits a second complex of proteins that includes axin, GSK3, and the protein APC. The axin/GSK-3/APC complex normally promotes the proteolytic degradation of the β-catenin intracellular signaling molecule. After this β-catenin destruction complex is inhibited, a pool of cytoplasmic β-catenin stabilizes, and some β-catenin is able to enter the nucleus and interact with TCF/LEF family transcription factors to promote specific gene expression. Several protein kinases and protein phosphatases have been associated with the ability of the cell surface Wnt-activated Wnt receptor complex to bind axin and disassemble the axin/GSK3 complex. Phosphorylation of the cytoplasmic domain of LRP by CK1 and GSK3 can regulate axin binding to LRP. The protein kinase activity of GSK3 appears to be important for both the formation of the membrane-associated Wnt/FRZ/LRP/DSH/Axin complex and the function of the Axin/APC/GSK3β-catenin complex. Phosphorylation of β-catenin by GSK3 leads to the destruction of β-catenin.

As an alternative to maintaining the OPCs in a progenitor cell state, the OPCs can be further differentiated into cells of the glial lineage through the control of other molecular mechanisms. In some embodiments, the OPCs generated using the methods of the invention are differentiated into myelinating oligodendrocytes 111 in vitro by withdrawal of FGF and PDGF and addition of T3 110. T3, triiodothyronine, is a thyroid hormone and affects almost every physiological process in the body, including growth and development, metabolism, body temperature, and heart rate. Production of T3 and its prohormone thyroxine (T4) is activated by thyroid-stimulating hormone (TSH), which is released from the pituitary gland. This pathway is regulated via a closed-loop feedback process. Elevated concentrations of T3, and T4 in the blood plasma inhibit the production of TSH in the pituitary gland; as concentrations of these hormones decrease, the pituitary gland increases production of TSH, and by these processes, a feedback control system is set up to regulate the amount of thyroid hormones that are in the bloodstream. T3 has profound effect upon the developing embryo and infants, affecting the lungs and influences the postnatal growth of the central nervous system. T3 also stimulates the production of myelin, the production of neurotransmitters, and the growth of axons, and is also important in the linear growth of bones.

In yet another alternative, the OPCs generated using the methods of the invention are differentiated into astrocytes 113 in vitro using a bone morphogenetic protein (BMP) and a JAK/STAT pathway activator 112. As described above, BMPs are a family of ligands that belong to the TGF beta superfamily, originally recognized for their ability to induce endochondral bone formation. One BMP particularly suited for use in the invention for differentiation of OPCs into astrocytes is BMP4. In human embryonic development, BMP4 is a signaling molecule required for the early differentiation of the embryo and establishment of a dorsal-ventral axis. BMP4 is secreted from the dorsal portion of the notochord, and acts in concert with SHH to establish a dorsal-ventral axis for the differentiation of later structures. In addition, BMP4 stimulates differentiation of overlying ectodermal tissue.

The janus kinase (JAK)-signal transducer and activator of transcription (STAT) pathway plays a critical role in the signaling of a wide array of cytokines and growth factors leading to various cellular functions, including proliferation, growth, hematopoiesis, and immune response. The binding of cytokines and growth factors to their corresponding receptors activates JAK, which then phosphorylates the receptor and STAT proteins on specific tyrosine residues. STATs then dimerize, translocate to the nucleus, bind to a consensus DNA sequence and initiate the transcription of target genes. Four JAK family kinases and seven STAT family members have been identified, some being ubiquitously expressed. Amino acid sequence diversity and tissue-specific distributions account for the diverse roles of STATs in response to extracellular cytokines Activators of JAK/STAT pathways include leukemia inhibitory factor (LIF), IL-6, cntf, CT-1, and OSM.

Using the methods of the invention outlined above, pluripotent cells can thus be differentiated into pure populations of clinically-relevant, OPCs that provide a tractable platform for defining the molecular regulation of oligodendrocyte development, exploring the causative cell and molecular defects that function in congenital disorders impacting the oligodendrocyte lineage, and for high-throughput drug screening. Moreover, the cell populations of the invention may be used in cell-based therapies to restore functional myelination. Alternatively, the OPCs can be further differentiated into myelinating oligdendrocytes and astrocytes that may be used in vitro or in vivo for drug screening or for cell-based therapies.

Cell Transplantation

Numerous methods for introducing the cells and cell populations of the invention into a subject may be used. An important aspect of the invention relates to a method of treating a subject having a condition mediated by a loss of myelin and/or an inability of oligodendrocytes to remyelinate nerve fibers by administering to the subject oligodendrocyte progenitor cells under conditions effective to treat the condition. For injection, cells of the pharmaceutical composition may be formulated in aqueous solutions, preferably in physiologically compatible buffers such as Hank's solution, Ringer's solution, or physiological salt buffer.

Administration of the pharmaceutical cell composition by injection includes intraparenchymal injections into the affected portion of the brain itself as well as introduction of the cells at a more distal site in the brain, brain stem or CNS, with the cells then migrating to the affected part of the brain. Administration typically involves cell doses ranging from $1 \times 10^4$ to $1 \times 10^9$, depending on the extent of desired remyelination. Dosage amount and interval may be adjusted individually to levels that are sufficient to effectively regulate remyelination by the implanted cells. Dosages necessary to achieve the desired effect will depend on individual characteristics and the route(s) of administration.

Depending on the severity and responsiveness of the condition to be treated, dosing may comprise a single administration or a plurality of administrations, with course of treatment lasting from several days to several weeks or until diminution of the disease state is achieved. The amount of the pharmaceutical cell composition to be administered will, of course, be dependent on the individual being treated, the severity of the affliction, the manner of administration, the judgment of the prescribing physician, etc. The dosage and timing of administration optimally will be responsive to a careful and continuous monitoring of the subject's changing condition. For example, a treated Multiple Sclerosis patient will be administered an amount of cells that is sufficient to alleviate the symptoms of the disease, based on the monitoring indications.

The cells of the present invention may be co-administered in a "cocktail" with therapeutic agents useful in treating neurodegenerative disorders, such as gangliosides; antibiotics, neurotransmitters, neurohormones, toxins, neurite promoting molecules; and antimetabolites and precursors of neurotransmitter molecules. Additionally, the cells of the invention may be co-administered with other cells.

Following transplantation, the cells of the invention preferably survive in the diseased area for a period of time (e.g., at least six months), such that a therapeutic effect is observed. In one aspect of the present invention, oligodendrocyte progenitor cells are administered to the subject after administration of radiation, e.g., to treat primary and metastatic tumors of the central nervous system.

In certain circumstances, including those in which the OPC or oligodendrocyte deficiency is coupled with a loss of neurons, it may be desirable to transplant mixed cell populations, such as mixtures of the OPC cell populations of the invention and neurons or neuronal precursors. The differentiated cells of the invention can thus be co-introduced with neurons or neuronal precursors, such as those produced as described in USSN 2010/0021437, which is incorporated herein by reference. In one aspect of the invention, a subject will be treated with both OPC or oligodendrocyte cell populations and neurons or neuronal precursor cells.

Generally, any method known in the art can be used to monitor success of transplantation, including both clinical and phenotypic indicators. For example, MRI can be used for visualizing brain white matter and studying the burden of demyelinating lesions as currently practiced for monitoring MS patients. Magnetic resonance spectroscopy measurement of N-acetyl-aspartate levels can be used to assess impact on local neuron/axon survival by using paramagnetic particles to label cells before transplantation, enabling cell dispersion to be tracked by MRI. Alternatively or in addition, magnetization transfer contrast can be used to monitor remyelination (Deloire-Grassin, J. Neurol. Sci., 178:10-16 (2000)). Serial neurophysiology monitoring techniques can also be used to assess improvement over time.

Additionally, electrophysiological measures of sensory and motor nerve conductivity, for example H-wave response, are classical methods used for monitoring neuropathies linked to demyelinating peripheral lesions (Lazzarini et al, Eds (2004) *Myelin Biology and Disorders* (Elsevier Academic Press)).

Other approaches to more generalized phenotypic neurophysiological assessment are described in Leocani et al., Neurol Sci., 21(4 Suppl 2):S889-91 (2000), which may be useful for interventions aimed at multifocal or more diffuse myelin repair. For example, demyelination causes alterations of stature (trembling, shivering) and locomotion, and children with leukodystrophies have motor and intellectual retardation. Improvement in these states may be assessed to monitor therapeutic success.

Applicable Disease States

The cell populations created using the methods of the invention can be used for research of demyelinating states, including the identification and development of drugs and therapeutic interventions in multiple disease states involving glial cells, and in particular diseases involving the CNS. Exemplary diseases that may be studied and for which therapeutic interventions may be identified using the cell populations of the invention are described in more detail below.

Multiple sclerosis (MS), a progressive, neurodegenerative disease of the CNS, occurs most often in a relapsing/remitting form, in which a period of demyelination is followed by a period of functional recovery (Weiner, Ann Neurol, 65:239-248 (2009)). The recovery stage involves remyelination via migration and maturation of OPCs (Chari, Int Rev Neurobiol, 79:589-620 (2007)). However, as the disease progresses, remyelination fails with progressive loss of function (Blakemore and Keirstead, J Neuroimmunol, 98:69-76 (1999)). Possible explanations for remyelination failure of intact axons include defects in OPC recruitment to the site of demyelination or defects in OPC differentiation into myelinating oligodendrocytes. Although studies indicate that both aspects of OPC biology are altered in MS, the molecular mechanisms that orchestrate these processes within the adult CNS are incompletely understood.

Other conditions mediated by a loss of myelin include an ischemic demyelination condition, an inflammatory demyelination condition, a pediatric leukodystrophy, mucopolysaccharidosis, perinatal germinal matrix hemorrhage, cerebral palsy, periventricular leukoinalacia, radiation-induced conditions, and subcortical leukoencephalopathy due to various etiologies, and mental illnesses, such as schizophrenia. Ischemic demyelination conditions include cortical stroke, Lacunar infarct, post-hypoxic leukoencephalopathy, diabetic leukoencephalopathy, and hypertensive leukoencephalopathy. Inflammatory demyelination conditions include multiple sclerosis, Schilder's Disease, transverse myelitis, optic neuritis, post-vaccination encephalomyelitis, and post-infectious encephalomyelitis. Pediatric leukodystrophy conditions include lysosomal storage diseases (e.g., Tay-Sachs Disease), Cavavan's Disease, Pelizaeus-Merzbacher Disease, and Crabbe's Globoid body leukodystrophy. An example of mucopolysaccharidosis is Sly's Disease. Radiation-induced conditions include radiation-induced leukoencephalopathy and radiation induced myelitis. Etiologies causing subcortical leukoencephalopathy include HIV/AIDS, head trauma, and multi-infarct states.

According to some features of the invention, the pharmaceutical cell compositions used in therapy may comprise oligodendrocytes and the medical condition is associated with insufficient myelination. According to still further features, the cells comprise astrocytes and the medical condition is selected from the group consisting of Alexander disease, epilepsy, Alzheimer's disease, spinal cord injury, traumatic brain injury and neurogenesis deficiencies. The subjects treated with pharmaceutical compositions comprises oligodendrocyte progenitor cells in accordance with the present invention are preferably mammals, more preferably humans and, most preferably, an adult or post-natal human.

Cell Populations as Research Tools for Drug Discovery and for Toxicity Testing

One significant use of the glial cell populations of the invention is as a research tool specifically for the discovery and development of therapeutic products for modulation of one or more biological processes involved in diseases, disorders and/or physiological processes such as neuronal repair. The cell-based research tools may be useful in various aspects of drug discovery and investigation, including without limitation initial identification of a drug candidate, confirmation of activity of a drug candidate, identification of activity for an existing pharmaceutical product, and/or toxicity of a drug or drug candidate. Another use of the cell-based compositions is as a research tool specifically used as a diagnostic tool to detect the presence or absence of molecules necessary for the modulation of a biological process involved in a disease or disorder. Thus, in one aspect, the invention includes research tools comprising the cell compositions of the invention, and uses of such research tools in the identification, investigation and/or confirmation of activity of selective binding agents that are useful as therapeutic agents. The present invention additionally encompasses binding agents that are isolated using the methods of the invention and uses of such binding agents in either a therapeutic or a diagnostic setting.

Thus, according to yet another aspect of the present invention there is provided a method of determining an effect of a treatment on CNS functionality, the method comprising subjecting cells of the present invention to a treatment or binding agent (e.g., drug, condition such as electrical treatment and an irradiation treatment); and determining at least one of a structural or functional phenotype of the treated cell as compared to an untreated cell, thereby determining an effect of the treatment on CNS functionality.

Determining the effect of a treatment of interest on the cells of the present invention can be used to identify and optimize treatments capable of restoring neural function via activity of glial cells, and hence can be used to identify and optimize drugs suitable for treating neural disorders. Determining the effect of a treatment directed to diseases of the CNS or any other tissue requiring neural functionality can be used to assess the toxicity of such clinical treatments on CNS function. Thus, this aspect of the invention can be utilized to determine the therapeutic and toxic effects of various treatments, such as drug treatments, on neural function via assessment of the activity of glial cells. Other aspects of the invention encompass using the cells or cell populations to obtain gene expression profiles and other changes before and after the cells or cell populations are subjected to a treatment.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

In general, the methods described herein and in the specific examples below are applicable to mammalian pluripotent cells; however, certain cells such as rodent embryonic stem cells and induced pluripotent stem cells, and various other mammalian stem cells (including human stem cells) may require a first step to differentiate these cells into epiblast or epiblast-like cells. In addition, the timing required for the various differentiation steps described herein may vary between mammals. For example, differentiation from pluripotent cells to neuroectoderm in mice may take from 2 to 5 days using the methods herein, where such differentiation in human pluripotent cells may take from 4 to 10 days. Similarly, differentiation from neuroectoderm to patterned neuroectoderm in mice may take from 1 to 2 days using the methods herein, where such differentiation in human neuroectoderm may take from 2 to 5 days.

Example 1

Differentiation of Pluripotent Cells to Neuroectoderm

All cells were cultured at 37° C. and 5% $CO_2$ unless otherwise noted. Individual EpiSC lines were isolated from mice of strains 129SvEv (EpiSC5 and EpiSC7 lines), (12901 line) and 129SvEv x ICR (EpiSC9 line), and maintained in vitro in EpiSC base medium supplemented with 10 ng ml$^{-1}$ PGF2 (R&D Systems, Minneapolis, Minn., 233-FB). Differentiation of EpiSCs to patterned neuroectoderm was a 5-day procedure with complete medium changes every day.

EpiSC base medium consisted of Knockout DMEM (Invitrogen, Carlsbad, Calif.) supplemented with 20% Knockout Serum Replacement (KSR; Invitrogen, Carlsbad, Calif.), 2 mM Glutamax (Invitrogen, Carlsbad, Calif.), 1×nonessential amino acids (Invitrogen, Carlsbad, Calif.) and 0.1 mM 2-mercaptoethanol (Sigma-Aldrich, St. Louise, Mo.). Neural base medium consisted of DMEM/F12 (Invitrogen, Carlsbad, Calif.; 11320) supplemented with 1×N2 (R&D Systems, Minneapolis, Minn.), 1×B-27 without vitamin A (Invitrogen, Carlsbad, Calif.) and 2 mM Glutamax. On day 0, EpiSCs were plated under standard passaging conditions in EpiSC base medium supplemented with 100 ng ml$^{-1}$ noggin (R&D Systems, Minneapolis, Minn.), 20 µM SB431542 (Sigma-Aldrich, St. Louis, Mo.; maintained as a 20 mM stock solution in DMSO) and 2 µM dorsomorphin (EMD; supplied as a 10 mM stock solution in DMSO). 0.1 µM LDN-193189 (Stemgent, San Diego, Calif.; maintained as a 1 mM stock solution according to the manufacturer's instructions) was used in place of dorsomorphin for some experiments. On day 1, cultures were fed with a 1:1 mixture of EpiSC base medium and neural base medium supplemented with 100 ng ml$^{-1}$ noggin, 20 µM SB431542 and 2 µM dorsomorphin. On day 2, cultures were fed with neural base medium supplemented with 100 ng ml$^{-1}$ noggin, 20 µM SB431542 and 2 µM dorsomorphin. On day 3, cultures were fed with neural base medium supplemented with 100 ng ml$^{-1}$ noggin. On day 4, cultures were fed with neural base medium supplemented with 100 ng ml$^{-1}$ noggin, 10 µM retinoic acid (Sigma-Aldrich, St. Louis, Mo.; maintained as a 20 mM stock solution in DMSO) and 200 ng ml$^{-1}$ SHH (R&D Systems; C24II).

Example 2

Differentiation of EpiSC-Derived, Patterned Neuroectoderm to OPCs

Day-5 patterned neuroectodermal cells were released from the culture dish using 1.5 mg ml$^{-1}$ collagenase IV (Invitrogen, Carlsbad, Calif.) and dissociated to a single cell suspension using TrypLE Select (Invitrogen, Carlsbad, Calif.). Cells were counted and plated at 4×104 cells cm−2 on Nunclon-Δ plates coated with 0.1 mg ml$^{-1}$ poly(L-ornithine) (Sigma-Aldrich, St. Louis, Mo.) followed by 10 µg ml$^{-1}$ laminin (Sigma; L2020). Cells were grown in OPC medium consisting of neural base medium supplemented with 20 ng ml$^{-1}$ FGF2, 20 ng ml$^{-1}$ PDGF-AA (R&D Systems, Minneapolis, Mo.) and 200 ng ml$^{-1}$ SHH, and fed every other day for 5 days. At this point cultures consisted of a highly pure population of proliferating OPCs.

Example 3

OPC Culture

Cultures of EpiSC-derived OPCs were maintained and expanded in neural base medium supplemented with 20 ng ml$^{-1}$ FGF2, 20 ng ml$^{-1}$ PDGF-AA and 200 ng ml$^{-1}$ SHH or 20 ng ml$^{-1}$ PDGF-AA, 200 ng ml$^{-1}$ SHH, 100 ng ml$^{-1}$ noggin, 10 µM dibutyryl cyclic-AMP sodium salt (Sigma-Aldrich, St. Louis, Mo.), 100 ng ml$^{-1}$ IGF-1 (R&D Systems, Minneapolis, Mo.), and 10 ng ml$^{-1}$ NT3 (R&D Systems, Minneapolis, Mo.) and fed every other day. OPCs were grown on Nunclon-Δ plates coated with poly(L-ornithine) and laminin Cells were passaged every 3-5 days with TrypLE Select and typically seeded at 2×10$^4$ cells cm$^{-2}$. OPCs could be readily frozen or thawed and were cryopreserved in DMEM supplemented with 10% FBS (Invitrogen, Carlsbad, Calif.) and 10% DMSO (Sigma-Aldrich, St. Louis, Mo.). For the cumulative OPC experiment, at 'passage 0' 4×10$^4$ cells cm$^{-2}$ were seeded. Subsequently, cells were passaged at 80-90% confluence and seeded at 2×10$^4$ cells cm$^{-2}$. Total cell number at each passage was counted with a hemocytometer. Rates of growth were determined at each passage and extended to the entire population of cells to yield a cumulative count.

Example 4

Differentiation of EpiSC-Derived OPCs

For differentiation of OPCs into oligodendrocytes, cells were plated at 2.2×10$^4$ cells cm$^{-2}$ and induced with neural base medium supplemented with 0.4 ng ml$^{-1}$ T3 (Sigma-Aldrich, St. Louis, Mo.), 200 ng ml$^{-1}$ SHH, 100 ng ml$^{-1}$ noggin, 10 µM dibutyryl cyclic-AMP sodium salt, 100 ng ml$^{-1}$ IGF-1 and 10 ng ml$^{-1}$ NT3. Attempts to modulate the outcome of this differentiation paradigm included treatments with Jag1 (R&D Systems, Minneapolis, Minn.), CHIR99021 (Stemgent, San Diego, Calif.), LIF (Millipore, Billerica, Mass.) and/or BMP4 (R&D Systems, Minneapolis, Minn.).

Example 4

Time-Lapse Imaging of EpiSC-Derived OPC Differentiation and Immunostaining

For live-cell imaging experiments, EpiSC-derived OPCs were plated onto poly(1-ornithine) and laminin-coated glass-bottom microwell dishes (MatTek, Ashland, Mass., P35G-1.5-14-C). Cells were seeded at a density of $3.1 \times 10^4$ cells $cm^{-2}$ in differentiation medium (T3, SHH, noggin, cAMP, IGF1 and NT3). After allowing the cells to adhere for 3 hours, images were collected every 10 minutes for up to 72 hours with a Hamamatsu Orca charge-coupled device (CCD) camera on an inverted microscope (Leica DMI6000B) outfitted with a precision scanning stage (Marzhauser, Wetslar, Germany) in a live-cell incubation chamber and cover (Pecon, Erbach, Germany) at 37° C. and 5% $CO_2$. Adaptive focus control was used to maintain multiposition focus stability over time. Movies were generated using Image Pro Plus and Adobe Premiere Pro CS5.

In vitro-cultured cells were prepared for immunostaining by fixation in 4% (vol/vol) paraformaldehyde (Electron Microscopy Sciences, Hatfield, Pa.) for 15 minutes and subsequent permeabilization for 10 minutes with 0.2% Triton X in PBS (pH 7.4). Cells were then blocked for non-specific binding with 10% normal goat serum (Abcam) or 10% normal donkey serum (Abcam, Cambridge, Mass.) in PBS for 1-2 hours at room temperature (21-24° C.). Primary antibodies were diluted in blocking solution and incubated with the samples either overnight at 4° C. or for 1 hour at room temperature. Samples were rinsed with PBS and incubated with the appropriate Alexa Fluor-labeled secondary antibodies (Invitrogen; 4 μg $ml^{-1}$) for 1 hour at room temperature. For visualization of nuclei, samples were incubated with 1 μg $ml^{-1}$ DAPI (Sigma-Aldrich, St. Louis, Mo.) in PBS for 5 minutes.

Live-cell staining was used for the cell-surface marker O4. Live cells were blocked with 10% normal goat serum and treated with O4 antibody for 20 min at 37° C. Cells were gently rinsed three times with warm neural base medium and fixed in 4% paraformaldehyde. Samples were rinsed with PBS and incubated with an Alexa Fluor-labeled secondary antibody (Invitrogen, Carlsbad, Calif.; 4 μg $ml^{-1}$) for 1 hour at room temperature. Cells were then permeabilized and stained with DAPI to visualize nuclei.

Primary antibodies used were antibodies to Oct3/4 (Santa Cruz, sc-5279; 0.4 μg $ml^{-1}$), Sox1 (R&D Systems, AF3369; 1 μg $ml^{-1}$), Pax6 (Covance, PRB-278P; 0.67 μg $ml^{-1}$), Olig2 (Millipore, Billerica, Mass., AB9610; 1:1,000), Nkx2.2 (DSHB, 74.5A5; 4.4 μg $ml^{-1}$), Sox10 (R&D Systems, AF2864; 2 μg $ml^{-1}$), O4 (1:10), GFAP (DAKO, Z0334; 0.58 μg $ml^{-1}$), βIII-tubulin (Covance, Tuj1; 0.2 μg $ml^{-1}$), and MBP (Covance, SMI-99P; 2 μg $ml^{-1}$ or Abcam, ab7349; 1:25). The Nkx2.2 (74.5A5) antibody developed by T. Jessell and S. Brenner-Morton was obtained from the Developmental Studies Hybridoma Bank developed under the auspices of the US National Institute of Child Health and Human Development and maintained by The University of Iowa.

For embryo tissue, embryonic day 11.5 (E11.5) embryos were fixed in 4% paraformaldehyde and cryosectioned. After antigen retrieval using sodium citrate buffer (10 mM sodium citrate and 0.05% Tween 20; pH 6.0), sections were blocked in 10% donkey serum with 0.2% Triton X for 2 hours. Sections were then stained in blocking solution using Olig2 (Millipore, Billerica, Mass., AB9610; 1:200) and Nkx2.2 (DSHB, 74.5A5; 8.8 μg $ml^{-1}$) antibodies overnight at 4° C. Alexa Fluor-labeled secondary antibodies (Invitrogen; 4 μg ml–1) were used for detection, and nuclei were visualized with DAPI.

For flow cytometry of PDGFRα and NG2, EpiSC-derived OPCs were collected from culture and blocked in 10% normal donkey serum for 30 minutes. Cells were then stained with allophycocyanin (APC)-conjugated PDGFRα (eBioscience, APA5; 4 μg $ml^{-1}$) and unconjugated rabbit polyclonal NG2 (Millipore, Billerica, Mass., AB5320; 1 μg $ml^{-1}$) antibodies for 30 minutes followed by incubation with Alexa Fluor-labeled secondary antibody (Invitrogen; 4 μg $ml^{-1}$) for 20 minutes. Isotype control antibodies were used as a staining control and to set gates (APC-conjugated rat IgG (eBioscience; 4 μg $ml^{-1}$) and normal rabbit IgG (Santa Cruz; 1 μg $ml^{-1}$) with Alexa Fluor-labeled secondary antibody (Invitrogen; 4 μg $ml^{-1}$)). Cells were analyzed on a BD FACSAria, and plots were generated with WinList 3D 7.0 software. Quadrant gates were set with isotype controls at less than 0.1% double-positive cells.

Example 5

Co-Culture Myelination Analysis

Primary neurons were obtained from the cortex of E17 mice. Following dissection, the cortex was incubated in 0.125% trypsin in Earle's balanced salt solution (EBSS) for 8 minutes at 37° C. and resuspended in 10 ml of DMEM containing 10% FBS. The cortex was centrifuged at 600 g for 2 minutes and resuspended in 1 ml of neural basal medium (NBM) containing 2% B27 (Invitrogen, Carlsbad, Calif.) and 0.25% Glutamax2. The cortex was then triturated through three glass pipettes of decreasing diameter, centrifuged, resuspended in supplemented NBM, and filtered through a 40-μm cell strainer (BD Biosciences, Franklin Lakes, N.J.). Cells were plated on chamber coverslips that had been coated with poly(d-lysine) and laminin and maintained at 37° C., 10% $CO_2$ for one week. EpiSC-derived OPCs were suspended in 1:1 (vol/vol) mixture of neurobasal and DMEM (ND) growth medium 2 and added to the neuron cultures. Cells were processed for immunofluorescence after 6 days of co-culture and analyzed using MBP (Abcam, Cambridge, Mass.) and βIII-tubulin (Tuj1; Neuromics, Edina Minn.) antibodies. Alexa fluor-labeled secondary antibodies (2 μg $ml^{-1}$) were used for detection and nuclei were visualized with DAPI.

Example 6

In Vivo Mylination Analysis

All experiments with animals were approved by the Institutional Animal Care and Use Committee of Case Western Reserve University. Early postnatal day 1-3 (P1-P3) shiverer (Mbpshi/shi) mice served as a host for the transplantation of EpiSC-derived OPC. Pups were anesthetized with sofluorane and $2.5 \times 10^5$ cells suspended in 1.5 μl of neural base medium were injected unilaterally to target the future corpus callosum at a rate of 0.5 μl $min^{-1}$. Injections were performed with a Hamilton syringe through the skull +0.5 mm right of midline and +0.5 mm anterior to bregma at a depth of 2 mm. Mice injected with EpiSC-derived OPCs as well as controls were killed at various time points to analyze myelination. Mice were deeply anaesthetized with rodent cocktail (ketamine, xylazine and acepromazine), perfused transcardially with 0.9% saline at room temperature and then perfused with ice-cold 4% paraformaldehyde. The brain was dissected and fixed for 2 hours in 4% paraformaldehyde then cryoprotected with sucrose. The cortex was frozen in optimal cutting temperature (OCT) medium on dry ice and 20 µm sections were cut on a Microm 525 cryostat. The sections were air-dried and then frozen. For fluorescent MBP staining, slides were thawed and allowed to dry, then rehydrated in PBS. Slides were treated with ice cold 95% methanol and 5% acetic acid for 7 minutes, rinsed in PBS and blocked in 10% goat serum for 1 hours at room temperature. Slides were then stained overnight for MBP (Covance; 2 µg ml$^{-1}$). Alexa Fluor-labeled secondary antibodies (2 µg ml$^{-1}$) were used for detection and nuclei were visualized with DAPI. Stained sections were mounted using Vectashield (Vector Labs) and imaged using a Zeiss LSM 510 META laser scanning confocal microscope. All images presented are maximum intensity projections of a z-dimension series consisting of 1.8-µm optical slices collected every 0.9 µm (optimal interval setting determined by LSM 510 software).

Example 7

Organotypic Slice Culture Myelination Analysis

The forebrain of P2-P4 shiverer or wild-type mice was dissected and 300 µm coronal slices were made on a Leica Vibratome. Slices were cultured as previously described in a DMEM-Basal Medium Eagle's base with 15% horse serum, modified N2 and PDGF-AA for 3 days. 2×10$^5$ EpiSC-derived OPCs was manually injected with a pulled glass pipette into the slices and grown for an additional 10 days in culture. Some OPC cultures were first lentivirally labeled with EGFP. Slices were fixed in 4% paraformaldehyde, treated with ice-cold 95% methanol and 5% acetic acid, and assayed for MBP expression (Covance; Jackson Labs, biotin-anti-mouse IgG; Vector Labs, ABC; Sigma, DAB). For lineage-tracing experiments, slices were assayed for NeuN expression (Millipore, Billerica, Mass., ABN78) and GFP (Invitrogen, Carlsbad, Calif. 3E6). To analyze the myelin ultrastructure, fixed and MBP-stained slices were then fixed (4% paraformaldehyde and 2% glutaraldehyde in 0.1 M cacodylate buffer, pH 7.4), incubated in 1% osmium tetroxide and stained en bloc in uranyl acetate. They were dehydrated and embedded in Poly/Bed 812 epoxy. Thick (1 µm) sections were cut and stained with toluidine blue. Thin (90 nm) sections were cut either en face or transversely, collected on 300-µm nickel grids, stained with toluidine blue and carbon-coated for electron microscopy. Toluidine blue-stained thick sections were imaged on a Leica DM5500B microscope at 100×, and toluidine blue-stained thin sections were imaged at 80 kV on a JEOL JEM-1200-EX electron microscope. Staining of sections for MBP before electron microscopy allowed for efficient targeting of the regions to be analyzed.

Example 7

Results

Figure 2:
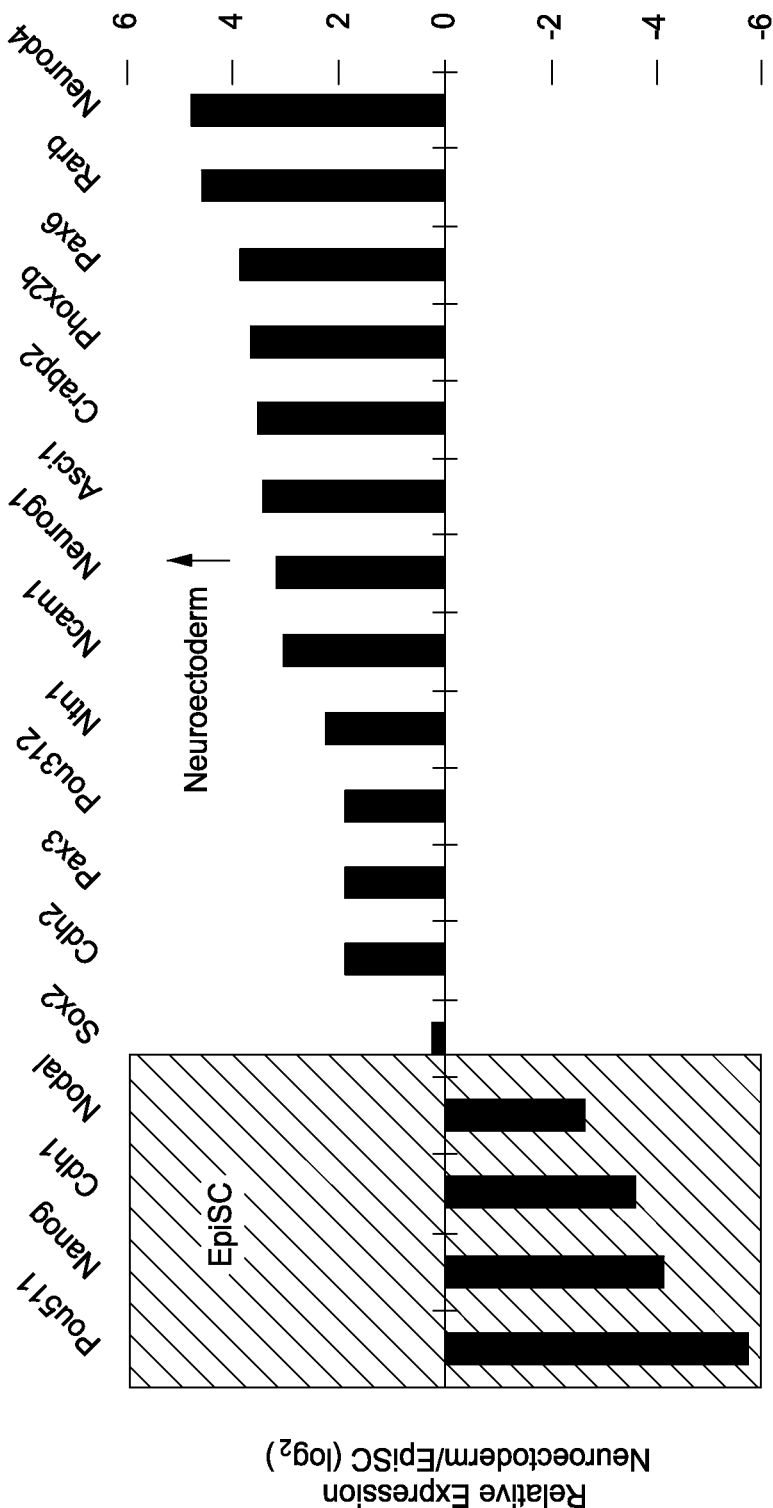
FIG. 2 is a bar chart illustrating results obtained of gene expression changes during transition of EpiSCs to neuroectoderm.

To differentiate epiblast stem cells (EpiSCs) into a neuroectodermal lineasge, EpiSCs were treated with SB431542, an inhibitor of Alk4, Alk5 and Alk7 (activin-nodal signaling); dorsomorphin or LDN-193189, inhibitors of Alk2, Alk3 and Alk6 (BMP signaling); and noggin, a BMP antagonist. In response, the EpiSCs rapidly downregulated the expression of pluripotency genes such as Pou5f1 (also known as Oct3/4), upregulated neuroectodermal genes such as Pax6 and Neurod4, and underwent morphological changes to form radially-organized patterned neuroectoderm (FIG. 2). This differentiation strategy was extremely robust and resulted in >99% of EpiSC colonies forming patterned neuroectoderm expressing both Pax6 and Sox1 (Pax6+ and Sox1+).

To test whether the induced patterned neuroectoderm behaved as un-induced neuroectoderm behaves, the induced EpiSC-derived patterned neuroectoderm were patterned in a region-specific manner. In the developing neural tube, specific cellular precursor domains are established by local signals from the surrounding tissues. In the developing spinal cord, OPCs first emerge from the ventral ventricular zone of the neural tube in response to sonic hedgehog (SHH) and other signals from the notochord and floor plate. Day-4 EpiSC-derived patterned neuroectoderm was treated for 1 day with specific concentrations of retinoic acid and SHH in the continued presence of noggin to pattern them in a region-specific way. This treatment resulted in the upregulation of OPC-relevant transcription factors Olig2 and Nkx2.2. The expression pattern of these factors in the patterned neuroectoderm mimicked the non-overlapping expression in the ventral ventricular zone of the developing mouse neural tube. Additionally, the EpiSC-derived patterned neuroectoderm expressed proper posterior-related Hox genes, thus confirming their spinal cord identity along the rostrocaudal axis. These results demonstrate that the provision of guiding developmental cues leads to proper specification and patterning of pluripotent cells into region-specific cells of the developing spinal cord in 5 days.

Figure 3:
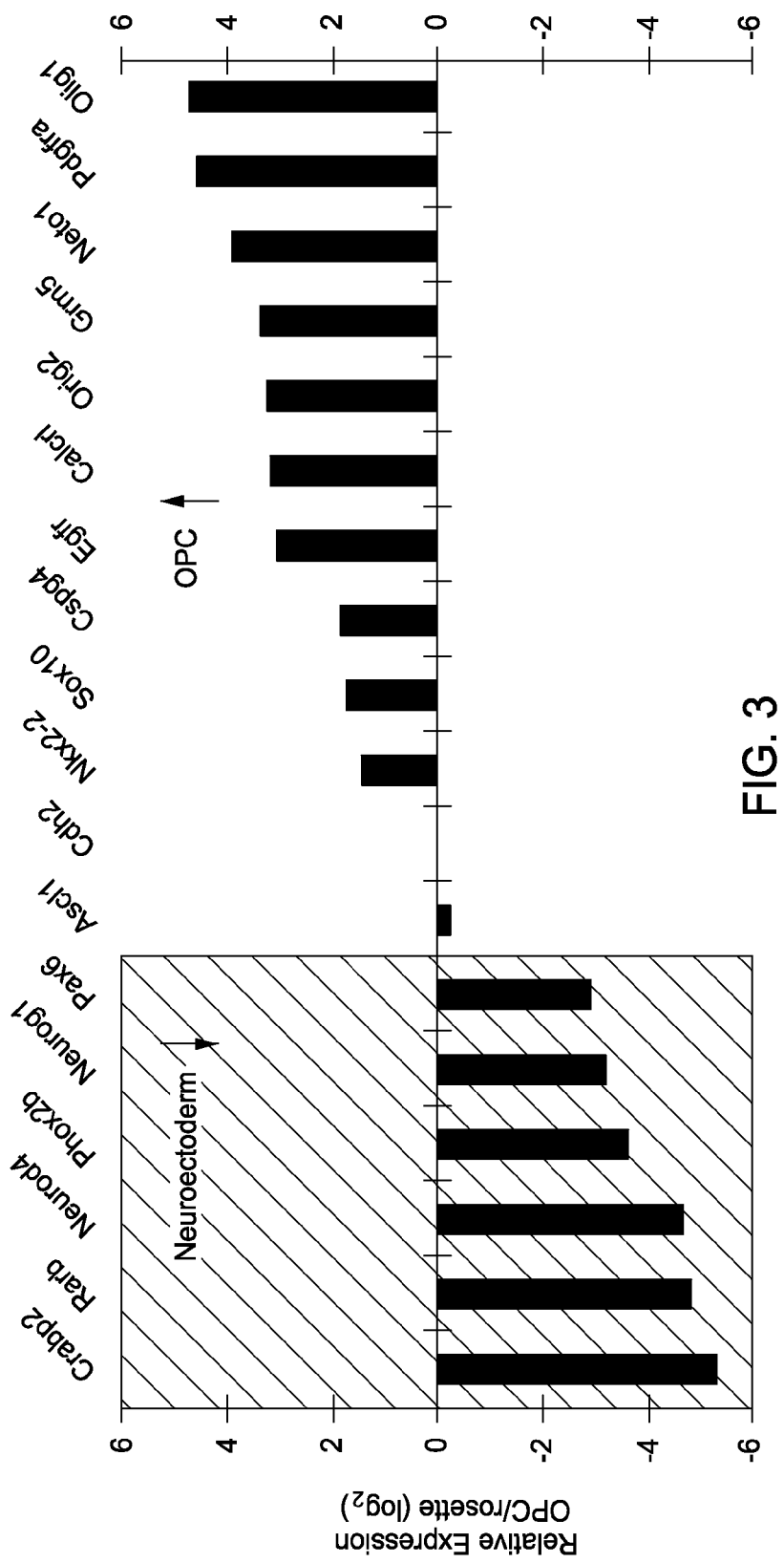
FIG. 3 is a bar chart illustrating results obtained of gene expression changes during transition of patterned neuroectoderm into OPCs.

Upon passage, the EpiSC-derived patterned neuroectoderm immediately gave rise to both βIII-tubulin+ neurons and presumptive OPCs that expressed Olig2 or Nkx2.2. These results recapitulate in vivo cell-specification events at the ventral ventricular zone of the developing spinal cord that are known to give rise to both neurons and OPCs. In these cultures, the neurons did not persist beyond the first 3 days of culture. However, the presumptive OPCs developed strong, co-expression of Olig2 and Nkx2.2 and rapidly proliferated in the presence of PGF2, PDGF and SHH to produce a confluent and nearly homogeneous population of cells in 5 days (10 days from initial differentiation of the EpiSCs). These EpiSC-derived OPCs exhibited a typical bipolar morphology and expressed transcription factors and cell surface markers such as Olig1, Olig2, Nkx2.2, Sox10, PDGFRα, EGFR and NG2 (Cspg4) consistent with their in vivo counterparts (FIG. 3). The EpiSC-derived OPCs were synchronous and highly pure as ~90% co-expressed the OPC surface markers NG2 and PDGFRα, as determined by flow cytometry, without selection or sorting. Additionally, these EpiSC-derived OPCs could be expanded for at least eight passages, yielding previously unobtainable numbers (>10$^{12}$ cells) of pure OPCs. To demonstrate the robust nature of this method, four independently-derived EpiSC lines (including lines from mice of different genders, strains and developmental stage) were simultaneously differentiated. All four cell lines differentiated efficiently into OPCs without any cell line-specific modifications.

Figure 4:
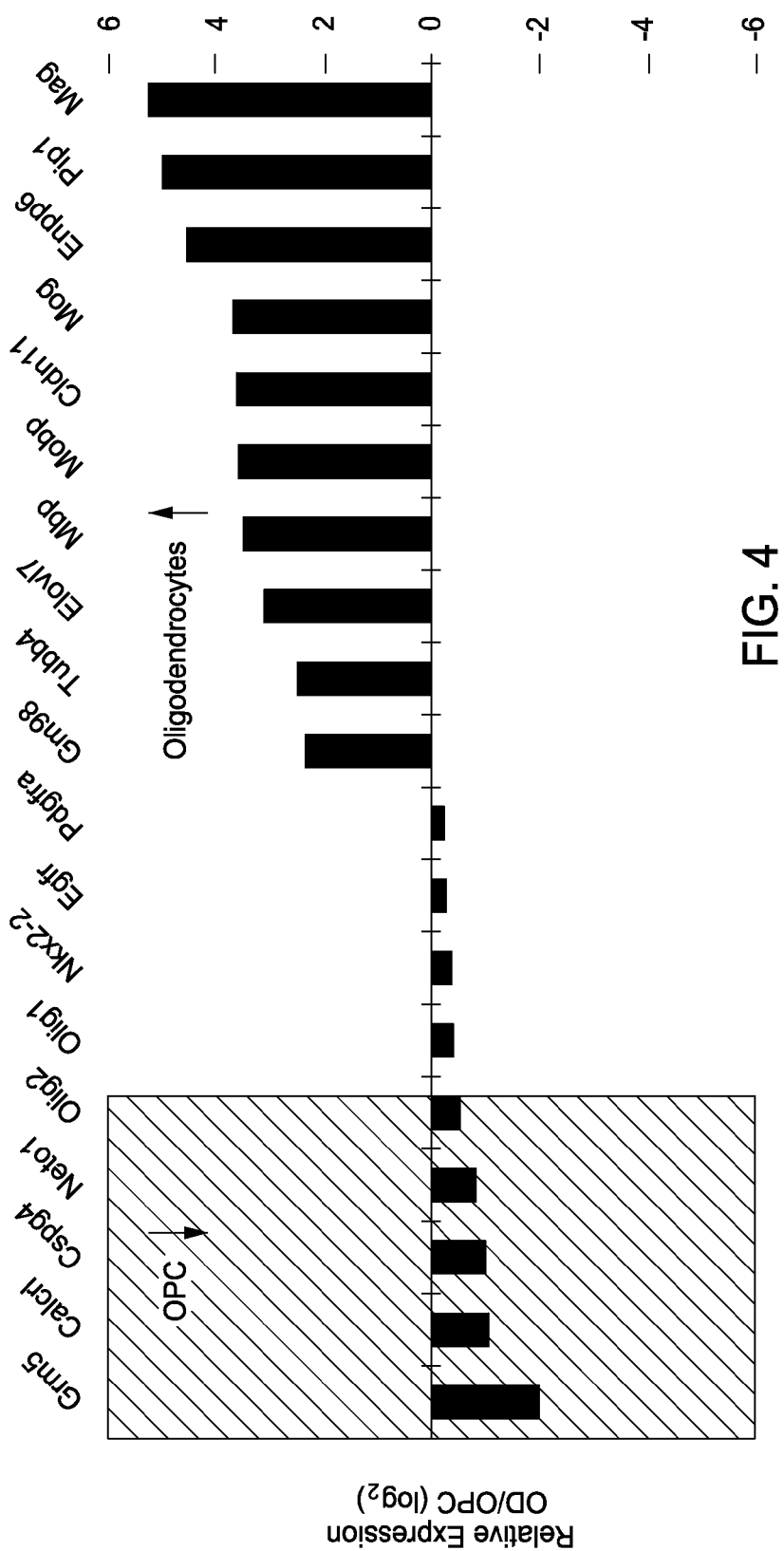
FIG. 4 is a bar chart illustrating results obtained of gene expression changes during transition of OPCs to oligodendrocytes.

To determine the differentiation capacity of the EpiSC-derived OPCs, the EpiSc-derived OPCs were treated with thyroid hormone (T3), which is known to be important both in vitro and in vivo in regulating the transition of OPCs into oligodendrocytes, in the absence of both FGF2 and PDGF-AA. These conditions caused the EpiSC-derived OPCs to stop proliferating and differentiate exclusively into oligodendrocytes over a 2-4 day time course. Undifferentiated OPCs did not express the oligodendrocyte cell-surface marker O4, but by day 2 of differentiation greater than 64% of the cells were strongly O4+ with a multiprocessed morphology and the rest remained Olig2+ OPCs (cells manually counted from random fields of independent lines, n>480 cells). By day 3, these O4+ oligodendrocytes had upregulated the classical and defining markers of bona fide oligodendrocytes such as myelin basic protein (Mbp), proteolipid protein 1 (P1p1), myelin-associated glycoprotein (Mag) and myelin oligodendrocyte glycoprotein (Mog) (FIG. 4). The differentiation was highly specific as neither GFAP+ astrocytes or βIII-tubulin+ neurons were observed. By day 4, the overwhelming majority of EpiSC-derived OPCs had become oligodendrocytes, though cell death and rare proliferation events made exact quantification challenging without large-scale time-lapse lineage analysis. To test the robust nature of this protocol, OPCs derived from four independent EpiSC lines were differentiated into oligodendrocytes, and there were no apparent differences in the efficiency or timing of differentiation. Freezing-thawing and extensive expansion of the EpiSC-derived OPC cultures did not alter their properties or ability to differentiate as all passages tested had highly-correlated global gene expression patterns and generated oligodendrocytes with similar timing and efficiency.

To examine the functional properties of EpiSC-derived OPCs, myelinogenic potential was measured by in vitro culture with neurons as well as in organotypic slice culture and in vivo by injection into the brains of congenitally hypomyelinated mice. For in vitro culture studies, EpiSC-derived OPCs were plated at low density onto cultures of mouse cortical neurons and allowed to differentiate. After 6 days, the EpiSC-derived OPCs had differentiated into MBP+ cells. Much of the MBP+ staining aligned with βIII-tubulin+ axons, which is suggestive of myelinogenic capacity. EpiSC-derived OPCs previously exposed to T3 did not produce MBP+ segments, which tracked with βIII-tubulin+ cells, suggesting temporal restriction of myelinogenic potential. To assess further the functionality of the EpiSC-derived OPCs, a tractable organotypic slice culture assay was utilized to evaluate myelinogenic potential. Injection of EpiSC-derived OPCs into coronal, forebrain slices of early postnatal shiverer (Mbpshi/shi) pups (which lack Mbp and compact myelin) resulted in substantial numbers of Mbp+ segments and compact myelin after 10 days. Transplanted EpiSC-derived OPCs specifically differentiated into oligodendrocytes and did not form neurons in the shiverer brain slices. The ability of EpiSC-derived OPCs to myelinate shiverer host axons in slice culture using both low- and high-passage number cells was assessed, with no evident differences.

To assess the myelinogenic capacity of EpiSC-OPCs in vivo, $2.5 \times 10^5$ cells were delivered into the future corpus callosum of newborn, immunocompetent shiverer (Mbpshi/shi) pups. The mouse brains were analyzed 3-7 weeks after injection and assayed for the presence of myelinated fibers in the brain. Many patches of MBP+ myelin sheaths were found in mice transplanted with EpiSC-derived OPCs but not in untransplanted controls. Additionally, EpiSC-derived OPCs appeared to migrate extensively in the host central nervous system as myelination at sites distant from the injection such as the contralateral striatum was observed. No teratomas or aberrant cellular growths were observed in any of the mice transplanted with EpiSC-derived OPCs at the time points evaluated. Taken together, these results demonstrate that EpiSC-derived OPCs function to produce compact myelin and provide a tractable source of cells to optimize cell-based transplantation strategies for myelin repair.

Figure 5:
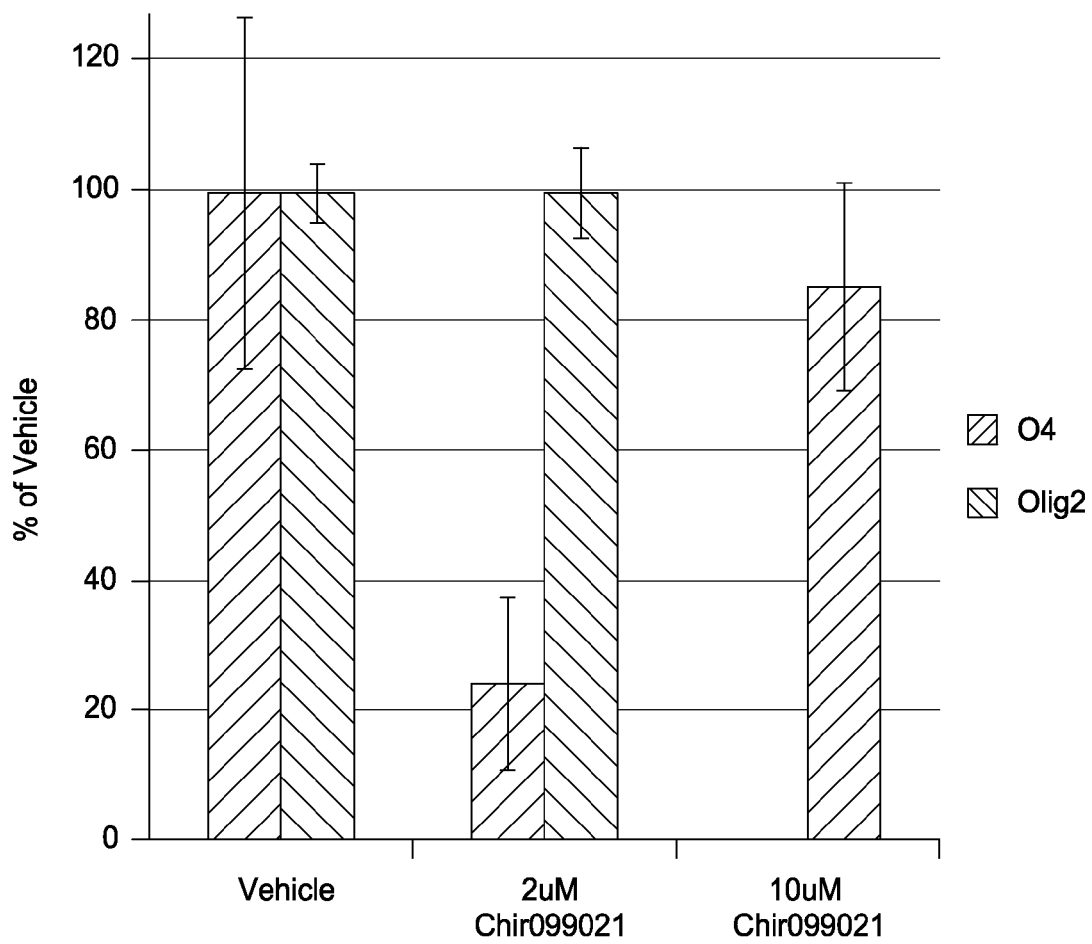
FIG. 5 is a bar chart illustrating the suppression of expression of mature oligodendrocyte markers upon treatment of OPCs with a GSK3β inhibitor Chir099021.

Next, the ability of extrinsic factors to modulate the differentiation of Epi-SC-derived OPCs was explored. As this invention allows for the scalable production of OPCs from pluripotent cells, it provides a platform to screen for molecules that influence the transition of OPCs into oligodendrocytes; particularly pertinent to disorders such as multiple sclerosis where NG2+ OPCs are present in or close to demyelinated lesions but generally do not remyelinate demyelinated axons. As a simple proof-of-principle for using the system to screen for compounds, EpiSC-derived OPCs were exposed to three different treatment regimens involving modulation of signaling pathways (Notch, Wnt-β-catenin and BMP) previously implicated in oligodendrocyte development or differentiation. Treatment of EpiSC-derived OPCs for 2 days with T3 differentiation medium in the presence of the Notch ligand Jagged1 (Jag1) did not impact the rate or number of O+ oligodendrocytes. Using a similar protocol, the role of GSK3β, a negative regulator of Wnt-β-catenin signaling, was tested by treating EpiSC-derived OPCs with the GSK3β inhibitor CHIR99021. This treatment resulted in a concentration-dependent inhibition of oligodendrocyte differentiation whereby cells remained Olig2+ OPCs and did not progress to O4+ oligodendrocytes (FIG. 5). These results suggest that canonical Wnt-β-catenin signaling, activated by inhibition of GSK3β, positively regulates the OPC state and blocks the transition to oligodendrocytes.

The final treatment involved exposure of EpiSC-derived OPCs to signaling cascades known to respecify OPCs in vitro into an alternate glial fate, astrocytes. Treatment of EpiSC-derived OPCs with BMP4 and leukemia inhibitory factor (LIF) resulted in the majority of cells undergoing morphological and gene expression changes including the upregulation of GFAP, indicative of respecification into astrocytes. These results demonstrate that scalable mouse pluripotent stem cell-based system provides a powerful way to screen for modulators of oligodendrocyte development and myelination.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. § 112, ¶6.

What is claimed is:

1. A composition comprising mammalian oligodendrocyte progenitor cells, the oligodendrocyte progenitor cells generated by providing a pluripotent cell; inducing development of the pluripotent cell into neuroectoderm by culturing the pluripotent cell in the presence of one or more inhibitors of an activin-nodal pathway and one or more inhibitors of a bone morphogenetic protein pathway; inducing development of patterned neuroectoderm by culturing the neuroectoderm in the presence of two or more of sonic hedgehog, retinoic acid and noggin; and inducing development of oligodendrocyte progenitor cells by culturing the patterned neuroectoderm cells in the presence of one or more of a fibroblast growth factor, a platelet-derived growth factor and sonic hedgehog.

2. The composition of claim 1, further comprising neurons or neuron precursors.

3. A composition comprising mammalian oligodendrocyte progenitor cells, the oligodendrocyte progenitor cells generated by providing a pluripotent cell; inducing development of the pluripotent cell into neuroectoderm by culturing the pluripotent cell in the presence of one or more inhibitors of an activin-nodal pathway and one or more inhibitors of a bone morphogenetic protein pathway; inducing development of patterned neuroectoderm by culturing the neuroectoderm in the presence of two or more of sonic hedgehog, retinoic acid and noggin; inducing development of oligodendrocyte progenitor cells by culturing the patterned neuroectoderm cells in the presence of one or more of a fibroblast growth factor, a platelet-derived growth factor and sonic hedgehog; and culturing the oligodendrocyte progenitor cells in the presence of an activator of Wnt-13-catenin signaling, wherein the oligodendrocyte progenitor cells remain in a progenitor cell state.

4. The composition of claim 3, further comprising neurons or neuron precursors.

5. The composition of claim 1, wherein the oligodendrocyte progenitor cells can be expanded for at least eight passages.

6. The composition of claim 3, wherein the oligodendrocyte progenitor cells can be expanded for at least eight passages.

7. A method of treating a medical condition of the central nervous system (CNS) in a subject comprising administering to the subject a therapeutically effective amount of the composition of claim 1.

8. A method of generating the composition of claim 3, comprising:
   providing a pluripotent cell;
   inducing development of the pluripotent cell into neuroectoderm by culturing the pluripotent cell in the presence of one of more inhibitors of an activin-nodal pathway and one or more inhibitors of a bone morphogenetic protein pathway;
   inducing development of patterned neuroectoderm by culturing the neuroectoderm in the presence of two or more of sonic hedgehog, retinoic acid and noggin;
   inducing development of oligodendrocyte progenitor cells by culturing the patterned neuroectoderm cells in the presence of one or more of a fibroblast growth factor, a platelet-derived growth factor and sonic hedgehog; and
   culturing the oligodendrocyte progenitor cells in the presence of an activator of Wnt-β-catenin signaling and maintaining the oligodendrocyte progenitor cells in cell culture.

9. The method of claim 8, wherein the activator of Wnt-β-catenin signaling is a GSK313 inhibitor.

10. The method of claim 9, wherein the GSK313 inhibitor is CHIR99021.

11. A method of treating a medical condition of the central nervous system (CNS) in a subject comprising administering to the subject a therapeutically effective amount of the composition of claim 3.

12. The method of claim 8, further comprising culturing the oligodendrocyte progenitor cells in the absence of FGF and PDGF and in the presence of the thyroid hormone T3.

* * * * *

UNITED STATES PATENT AND TRADEMARK OFFICE
CERTIFICATE OF CORRECTION

PATENT NO.        : 9,969,974 B2
APPLICATION NO.   : 14/949578
DATED             : May 15, 2018
INVENTOR(S)       : Paul J. Tesar et al.

It is certified that error appears in the above-identified patent and that said Letters Patent is hereby corrected as shown below:

In the Claims

At Column 25, Line 27, Claim 3, please replace the term "Wnt-13-catenin" with "Wnt-β-catenin".

Signed and Sealed this
Twenty-sixth Day of June, 2018

Andrei Iancu
*Director of the United States Patent and Trademark Office*